US006337996B1

(12) United States Patent
Legay et al.

(10) Patent No.: US 6,337,996 B1
(45) Date of Patent: *Jan. 8, 2002

(54) ACTIVE IMPLANTABLE MEDICAL DEVICES WITH REFRACTORY PERIOD MANAGEMENT

(75) Inventors: Thierry Legay, Fontenay Les Briis; Jean-Luc Bonnet, Montrouge; Anne Bouhour, ville D'Avray, all of (FR)

(73) Assignee: Ela Medical S.A., Montrouge (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/326,207

(22) Filed: Jun. 4, 1999

(30) Foreign Application Priority Data

Jun. 5, 1998 (FR) .............................. 98 07055

(51) Int. Cl.⁷ .............................................. A61N 1/362
(52) U.S. Cl. ............................................. 607/9; 607/13
(58) Field of Search ........................... 607/5, 6, 9, 13

(56) References Cited

U.S. PATENT DOCUMENTS 4,779,617 A  * 10/1988  Whigham ..................... 607/9
4,974,589 A    12/1990  Sholder ......................... 128/419
5,388,586 A    2/1995   Lee et al. ..................... 128/704
5,540,725 A    7/1996   Bornzin et al. ................ 607/9
5,776,167 A  * 7/1998   Levine et al. .................. 607/9

FOREIGN PATENT DOCUMENTS

EP    0318304 A2    5/1989    ........... A61N/1/365
EP    0562237 A1    9/1993    ... A61N/1/368 ...

* cited by examiner

Primary Examiner—George R. Evanisko
(74) Attorney, Agent, or Firm—Orrick, Herrington & Sutcliffe LLP

(57) ABSTRACT

An active implantable medical device with a sophisticated management of the refractory periods. Such devices typically include a detection circuit and a stimulation circuit and a circuit which applies a refractory period to the detection circuit, including an absolute refractory period (ARP), which can be fixed or pre-programmed, and a relative refractory period (RRP), which is variable. The relative refractory period includes a succession of elementary periods (X) of a fixed or programmable duration, which elementary period is further subdivided into sub-periods (Y) such that an elementary period X is retriggered or restarted at the end of a sub-period Y if a residual potential of a level higher than a given threshold is detected at output of the detection circuit during that sub-period. In the absence of a detected residual potential being detected during the successive sub-periods comprising the elementary period, then the refractory period ends.

19 Claims, 1 Drawing Sheet

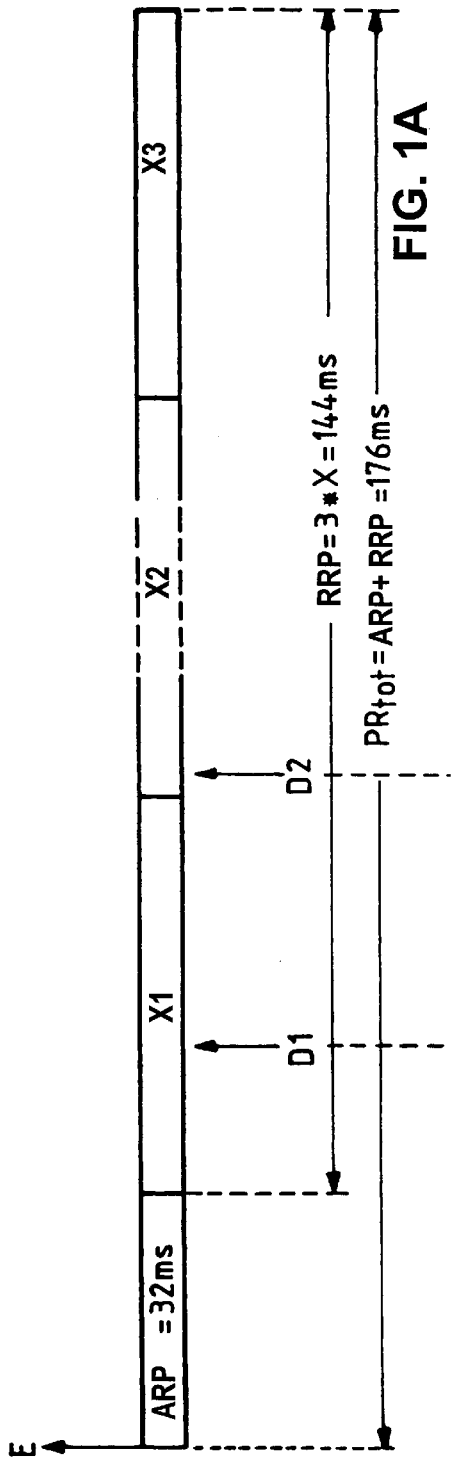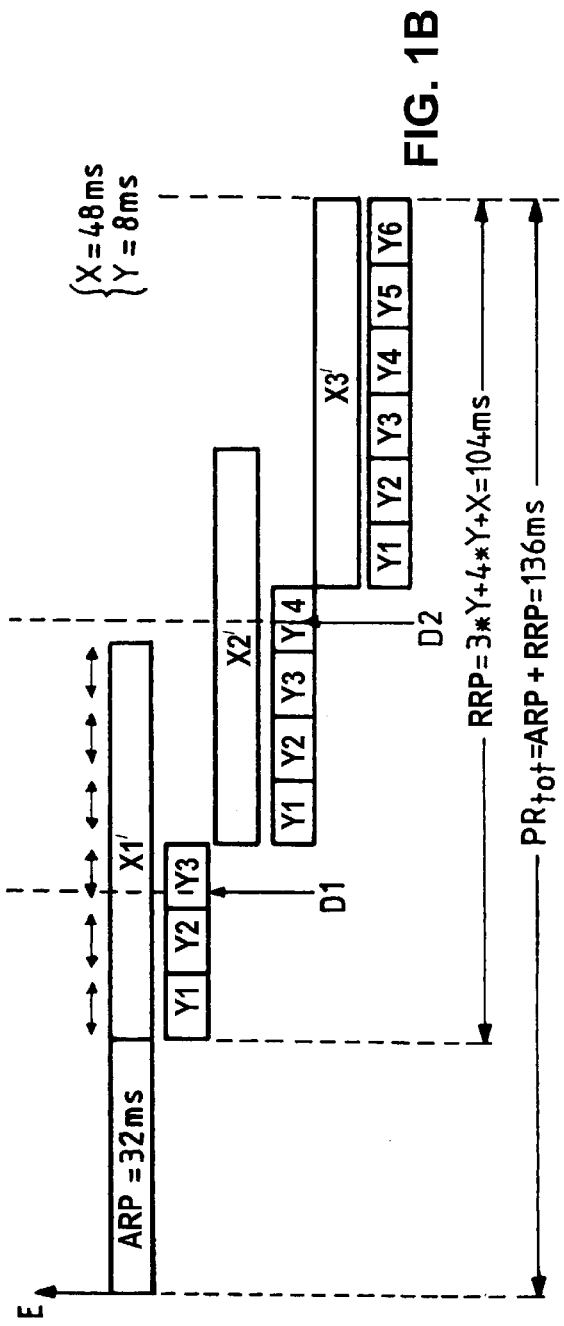

ACTIVE IMPLANTABLE MEDICAL DEVICES WITH REFRACTORY PERIOD MANAGEMENT

FIELD OF THE INVENTION

The present invention relates to "active implantable medical devices," as defined the Jun. 20, 1990 directive 90/385/CEE of the Council of the European Communities, and more particularly to pacemaker devices (for the treatment of bradycardia), defibrillators and/or cardiovertors (for the treatment of tachycardia), as well as resynchronizing "multisite" devices (for the treatment of desynchronization between cardiac cavities).

BACKGROUND OF THE INVENTION

The devices for which the present invention is useful include a circuit or means for the detection of cardiac activity, i.e., detection of a spontaneous depolarization of the myocardium, and a circuit or means for effecting the stimulation of the myocardium. During and after each activation of the stimulation circuit, which may be detected by monitoring the stimulation circuit or by sensing the myocardium potential, it is envisaged to provide a period known as the "refractory period", during which there is a disconnection or "blanking" of the detection circuits. This is done so as to mask any disturbances of the amplifiers in the detection circuit immediately following the delivery of a stimulation to the myocardium. Such disturbances are, for example, due to the flow of the electrical charges at the electrode/myocardium interface. Typically, the stimulation event is detected by monitoring the operation of the stimulation circuit, knowing that an escape interval has expired and noting that the stimulation capacitor discharges. This also permits applying the refractory period to prevent saturation of the detection circuit amplifiers based on the stimulation pulse.

A long refractory period makes it possible to obtain a good safety margin for the elimination (i.e., non-detection) of these disturbances. However, it also presents the disadvantage of masking any detection of the signals emitted by the myocardium for a relatively long period of time.

It is important to be able to listen to the spontaneous rate/rhythm of the patient as soon as possible after a stimulation, in order to detect most precociously, i.e., as soon as possible, a possible depolarization wave revealing a spontaneous activity of the myocardial cells. This early listening makes it possible to carry out, for example, very precise control algorithms for controlling the rate of the heartbeat, thus giving rise to a more physiological behavior of the implanted medical device (also called a "prosthesis") or to allow a reduction of energy consumption by delivering only suitable stimulation.

This early detection also is used to control advantageously the operation of certain other known algorithms used in such active implantable medical devices, such as the algorithms of fallback of the pacing rate (also referred to as "repli"), rate smoothing, etc. In addition, the detection of the spontaneous ventricular rhythm, in particular the analysis of its stability, is in certain implantable defibrillators an essential parameter in the release of a shock therapy.

To take account of the various possible situations, the refractory period is generally made variable, with a fixed or programmed portion known as the "absolute refractory period" (ARP), and a variable portion known as the "relative refractory period" (RRP). One can, for example, vary the RRP according to the programmed stimulation amplitude. This is because the disturbance which one wants not to respond to is shorter in time in the case of a stimulation with a low energy level (for example 1.5 V) than in the case of a stimulation with a higher energy (for example 5.0 V).

Other techniques, for example, the technique referred to in U.S. Pat. No. 4,974,589 and the technique used in the CHORUS brand pacemakers available from ELA Médical, Montrouge, France, the assignee of the present invention, involve detecting in the course of an ARP a presence of a residual potential at the output of the primary amplifiers of the detection circuits of the endocardium cardiac signal. If a residual potential is detected, one then prolongs the ARP by one predetermined duration, hereafter indicated as an "elementary period", and this elementary period is repeated (restarted or "recycled" or "retriggered") as long as a post-stimulation residual potential appears at output of the detection circuit amplifiers.

When the detected residual potential is lower than a given threshold, the automatic recycling of the elementary period ceases, and at the end of the period the system then passes to a mode of listening for the cardiac signals. In other words, the blanking provided by the refractory period is ended.

OBJECTS AND SUMMARY OF THE INVENTION

It is an object of the present invention to provide an improvement to the active implantable medical devices of the aforementioned type, an improvement which allows for a very fine management of the duration of the relative refractory period RRP so as to reduce the RRP to a minimum time, and thus maximize the duration of listening for the spontaneous rhythm of the patient. It is a further object to implement such an operation to carry out in an optimal way the various control algorithms of the device.

A representative device for use with the present invention is of the type which is described in U.S. Pat. No. 4,974,589. This device is provided with a refractory period applied to the detection circuits after activation of the stimulation circuit. The refractory period includes a fixed or programmed absolute refractory period (ARP), and a variable, relative refractory period (RRP). The relative refractory period includes a succession of elementary periods of fixed or programmable duration which are repeated or retriggered, in response to a detected occurrence of a residual potential of a level higher than a given threshold at an output of the detection circuit, until one elementary period occurs without a detected residual potential occurring.

According to one aspect of the invention, the refractory period is provided with a relative refractory period such that on each retriggering of an elementary period of the relative refractory period, a succession of sub-periods of a given duration are applied to correspond to the elementary period, such that each sub-period is shorter than that one elementary period. More preferably, during each sub-period, the possibility of an occurrence of a residual potential is examined. In the event of a detected residual potential event, the elementary period is then retriggered to begin again as of the end of the sub-period during which the residual potential event was detected. In the absence of a detected residual potential, the sub-period will continue to its end and then be retriggered, if necessary, until the end of the elementary period (that is until all of the sub-periods have occurred) at which time the refractory period will be over.

The duration of the sub-period is advantageously selected to be a submultiple of the duration of the elementary period. In one preferred embodiment, the ratio between the duration of the sub-period and that of the elementary period is at least 2:1, more preferably at least 6:1. However, the sub-periods may be non-uniform in duration.

BRIEF DESCRIPTION OF THE DRAWINGS

Other characteristics, advantages and features of the present invention will become apparent to a person of ordinary skill in the art in view of the following detailed discussion of the invention, made with reference to the annexed drawings in which FIGS. 1(a) and (b) represent two chronograms showing the decomposition of a refractory period, respectively according to the prior art and to a preferred embodiment in accordance with the present invention.

DETAILED DESCRIPTION OF THE DRAWINGS

With reference to the drawings, FIG. 1(a) corresponds to a refractory period as defined by a known prior art device, for example, the Model CHORUS pacemaker of ELA Médical, just after a cardiac event E corresponding to a stimulation. The prior art device applies one absolute refractory period ARP, typically of 32 ms, during which no detection can affect the behavior of the cardiac pacemaker prosthesis. At the end of the ARP, the refractory period then continues with a relative refractory period RRP during which those detections which do occur do not have any influence on the behavior of the control algorithms of the prosthesis. The detections do, however, cause a retriggering of an RRP for one elementary period, typically X=48 ms, until one of the subsequent elementary periods proceeds to its conclusion without any intervening detection of a residual potential therein.

Thus, in the illustrated prior art example of FIG. 1(a), a detection (i.e., a residual or any potential greater than a predetermined threshold) D1 intervenes during the first elementary period X1 which causes a re-triggering of the period X at the conclusion of the preceding period X1, and thus the prolongation of the RRP by a new period X2. The second detection D2 occurring during the second elementary period X2 causes another re-triggering of the elementary period X for a third elementary period X3 commencing at the end of the period X1. No detection D being detected during the third elementary period X3, the prosthesis then passes to a mode of listening for spontaneous cardiac signals.

The relative refractory period is thus, in this example, RRP=3*X=144 ms, and the total duration for the refractory period PRtot=ARP+RRP=32+144=176 ms. It will be noted that, in the illustrated example, the second detection (D2) occurred at a relatively early time during the second elementary period X2, so that the RRP continued for a duration almost equal to 2*X between the last detection of a residual potential (D2) and the beginning of the phase of listening for the cardiac signals.

The present invention advantageously proposes to improve the mode of determination of the RRP so as to curtail this RRP time, and to make it possible to pass sooner to the mode of listening for the cardiac signals. With this intention, as illustrated in FIG. 1(b), after the ARP a first elementary period X is started to initiate the RRP. But in this case the re-triggering of the elementary period X by a detection D is operated in a different way. After having started the elementary period X, the device defines a succession of sub-periods Y and examines whether, during each one of the sub-periods, a residual potential D is detected or not. The duration Y is selected to be substantially shorter than the duration of the elementary period X. Preferably, Y is a submultiple of X, for example Y=X/6=8 ms.

If a detection D intervenes during the one of these sub-periods Y (for example, the detection D1 occurs during the third sub-period Y3 of the first elementary period X1'), then the elementary period X is retriggered as period X2' at the end of this sub-period Y3, without waiting until the end of the elementary period X1' then in progress to restart the next elementary period.

Thus, in the example illustrated on FIG. 1(b), the second elementary period X2' is started, 3*Y=24 ms after the beginning of the RRP, instead of 48 ms after, as with the known technique on the corresponding FIG. 1(a).

The same process of detection/re-triggering is realized during the second elementary period X2': Thus, if a detection D2 intervenes during the fourth sub-period Y4 of elementary period X2', the elementary period X3' is retriggered at the end of this fourth sub-period Y4. The RRP then ends when one complete elementary period X passes (or, in other words, in this embodiment six consecutive sub-periods Y pass) without any residual potential being detected.

In the illustrated example, the RRP thus concludes at the end a total time of 3*Y+4*Y+X=104 ms, for a total refractory period duration of PRtot=ARP+RRP=32+104=136 ms for the refractory period. One thus sees that, for detections D1 and D2 occurring at the same moment, in this particular example, one has, according to the advantageous technique of the invention, reduced the duration of the RRP by 40 ms. This corresponds to a 28% difference, thus allowing the device to pass much earlier to a mode of listening for spontaneous signals of the heart.

The values for the ARP, elementary period X and subperiod Y are preferably programmable for a given prosthesis, or even for a particular operating mode of a prosthesis, and possibly (but not necessarily) programmable by the therapist (e.g., physician).

Further, it will be understood by a person of ordinary skill in the art that if the device relates to a plurality of cavities, the technique of the invention solves all the cases of blanking protection in a general way, and it is not necessary to provide specific protections to the different cavities, such as of the type known as "post-atrial stimulation ventricular blanking".

Indeed, the last event appearing in a period of listening in an unspecified cardiac cavity will be able to recycle the generation of the elementary periods X of the RRP in all the cardiac cavities having a system of detection. In all the cases, the final duration of the refractory period, for each cavity independently detected, will always be adequate and minimal since it will be based on the presence or absence of parasitic potentials at the output of its detection circuit. In other words, the duration of the RRP for a particular cavity depends only on an accumulation in that cavity of the post-stimulation potentials created by any of the stimulated/ detected events occurring anywhere in the heart.

This technique also makes it possible to take into account all the electromagnetic disturbances, internal or external, concerning the cavity considered. Indeed, re-triggering persists in the presence of electric noise, maintaining the prosthesis in a refractory state as long as the disturbance is present.

In this respect, the parameters X and Y defining the RRP can be programmed to render the prosthesis refractory to noises whose frequency exceeds 20 Hz, as specified by the European standard EN 45 502. For example, with one retriggerable elementary period X=48 ms with sub-periods Y=8 ms, a prosthesis will pass to operate in an asynchronous mode if it appears that persistent noise of a frequency higher than 20.8 Hz is detected.

It also will be noted that the system according to the invention can be easily realized with a dedicated or hard-wired logic circuits, which makes it possible to have a lower energy consumption of the device, as compared to an implementation in software with a microprocessor, which is equally possible.

One skilled in the art will appreciate that the present invention can be practiced by other than the described embodiments, which are presented for purposes of illustration and not of limitation.

We claim:

1. An active implantable medical device, comprising:
   a stimulation circuit to stimulate the myocardium;
   a detection circuit to detect an activity of the myocardium including an operation of the stimulation circuit and a residual potential event having a potential greater than a threshold potential; and
   means for applying a refractory period to the detection circuit in response to a detected operation of the stimulation circuit, said refractory period having an absolute refractory period and a relative refractory period, the relative refractory period further comprising at least one elementary period corresponding to a time period during which the absence of a residual potential event defines the end of the relative refractory period, said elementary period comprising a number of successive sub-periods, each sub-period having a duration that is shorter than said elementary period, and
   means for retriggering the elementary period in response to a detected residual potential event during said elementary period,
   wherein the means for applying the refractory period:
   a) produces, on each retriggering of an elementary period, a sequence of said successive of sub-periods,
   b) examines each triggered sub-period for an occurrence of a possible residual potential, and
   c1) in response to a detected residual potential event, retriggers the elementary period to restart at the end of the sub-period during which the residual potential event was detected, and
   c2) in the absence of a detected residual potential event, retriggers the sub-period to restart as of the end of the sub-period during which the residual potential event was not detected until the end or the sequence of sub-periods defining said elementary period.

2. The device of claim 1, wherein each sub-period has a first duration and the elementary period has a second duration and the first duration of the sub-period is a submultiple of the second duration of the elementary period.

3. The device of claim 1 wherein the sub-period has a duration and the elementary period has a duration and wherein the durations of the sub-period and the elementary period form a ratio of at least 2:1.

4. The device of claim 3 wherein the ratio between the durations of the sub-period and the elementary period is at least 6:1.

5. The device of claim 1 wherein the absolute refractory period is a fixed value.

6. The device of claim 1 wherein the absolute refractory period is a preprogrammed value.

7. The device of claim 1 wherein the elementary period is a fixed value.

8. The device of claim 7 wherein the sub-period is a fixed value.

9. The device of claim 1 wherein the elementary period is a preprogrammed value.

10. The device of claim 9 wherein the sub-period is a preprogrammed value.

11. The device of claim 9 wherein the means for applying the refractory period is coupled to the detection circuit output and wherein said residual potential corresponds to the detection circuit output.

12. An active implantable medical device, comprising:
    a stimulation circuit to stimulate the myocardium;
    a detection circuit to detect an activity of the myocardium including an operation of the stimulation circuit and a residual potential event having a potential greater than a threshold potential; and
    means for applying a refractory period to the detection circuit in response to a detected operation of the stimulation circuit, said refractory period having an absolute refractory period and a relative refractory period, the relative refractory period further comprising at least one elementary period corresponding to a time period during which the absence of a residual potential event defines the end of the relative refractory period, said elementary period comprising a number of successive sub-periods, each sub-period having a duration that is shorter than said elementary period, and
    means for retriggering the elementary period in response to a detected residual potential event, wherein the means for applying the refractory period:
    a) produces, on each retriggering of an elementary period, a sequence of said successive sub-periods, the sum of the sub-period periods equaling the duration of the elementary period,
    b) examines each sub-period for an occurrence of a possible residual potential, and
    c1) in response to a detected residual potential event, retriggers the elementary period to restart at the end of the sub-period during which the residual potential event was detected, and
    c2) in the absence of a detected residual potential event, triggers the next sub-period in said sequence of successive sub-periods at the end of the sub-period during which the residual potential event was not detected, until the end of the elementary period.

13. The device of claim 12 wherein the absolute refractory period is a fixed value.

14. The device of claim 12 wherein the absolute refractory period is a preprogrammed value.

15. The device of claim 12 wherein the elementary period is a fixed value.

16. The device of claim 15 wherein each sub-period is a fixed value.

17. The device of claim 12 wherein the elementary period is a preprogrammed value.

18. The device of claim 17 wherein each sub-period is a preprogrammed value.

19. The device of claim 17 wherein the means for applying the refractory period is coupled to the detection circuit output and wherein said residual potential corresponds to the detection circuit output.

* * * * *

UNITED STATES PATENT AND TRADEMARK OFFICE
CERTIFICATE OF CORRECTION

PATENT NO. : 6,337,996 B1
DATED : January 8, 2002
INVENTOR(S) : Thierry Legay et al.

It is certified that error appears in the above-identified patent and that said Letters Patent is hereby corrected as shown below:

Column 1,
Line 7, delete "the" and insert -- in the -- therefor;

Column 4,
Line 3, delete "during the" and insert -- during -- therefor;

Column 5,
Line 6, delete "circuits" and insert -- circuit -- therefor;
Line 7, delete "consumption of" and insert -- consumption by -- therefor;
Line 38, delete "successive of" and insert -- successive -- therefor; and
Line 49, delete "end or" and insert -- end of -- therefor;

Signed and Sealed this

Twenty-eighth Day of June, 2005

JON W. DUDAS
*Director of the United States Patent and Trademark Office*